United States Patent

Chen et al.

(10) Patent No.: US 6,541,256 B1
(45) Date of Patent: Apr. 1, 2003

(54) GROWTH MEDIUM FOR HUMAN CORNEAL ENDOTHELIAL CELLS

(75) Inventors: Ko-Hua Chen, Taipei (TW); Nancy C. Joyce, Marlborough, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 09/913,218

(22) PCT Filed: Feb. 11, 2000

(86) PCT No.: PCT/US00/03531

§ 371 (c)(1),
(2), (4) Date: Sep. 14, 2001

(87) PCT Pub. No.: WO00/47040

PCT Pub. Date: Aug. 17, 2000

Related U.S. Application Data

(60) Provisional application No. 60/119,788, filed on Feb. 11, 1999.

(51) Int. Cl.⁷ ............................... C12N 5/00; C12N 5/02
(52) U.S. Cl. ..................... 435/405; 435/404; 435/325
(58) Field of Search ..................... 424/78.04, 85.1; 435/405, 404, 1, 240.2, 240.3, 325; 514/12

(56) References Cited

U.S. PATENT DOCUMENTS

| | | | | |
|---|---|---|---|---|
| 4,959,319 A | | 9/1990 | Skelnik et al. ............ 435/240.2 |
| 4,973,493 A | * | 11/1990 | Guire ............................. 472/2 |
| 5,045,454 A | | 9/1991 | Bertheussen ................. 435/29 |
| 5,332,671 A | | 7/1994 | Ferrara et al. ........... 435/240.1 |
| 5,407,669 A | * | 4/1995 | Lindstrom et al. ....... 424/78.04 |
| 5,589,451 A | | 12/1996 | Wilson ........................... 512/2 |

OTHER PUBLICATIONS

Kruse et al. Growth Factors Modulate Clonal Growth and Differentiation of Cultured Rabbit Limbal and Corneal Epithelium; Investigative Ophthalmology & Visual Science, 1993, vol. 34, No. 6, pp. 1963–1976.*

* cited by examiner

*Primary Examiner*—Christopher R. Tate
*Assistant Examiner*—Patricia Patten
(74) *Attorney, Agent, or Firm*—Weingarten, Schurgin, Gagnebin & Lebovici LLP

(57) ABSTRACT

A human cell growth medium formulation for culturing human cells of neural crest origin, most preferably corneal endothelial cells, or for accelerating the growth and proliferation of human cells of neural crest origin is disclosed. The formulation for the nutrient medium of the invention includes nerve growth factor, preferably at a concentration of 1–100 ng/ml and most preferably 20 ng/ml. The growth medium formulation preferably also includes epidermal growth factor (preferably at a concentration of 1–200 ng/ml and most preferably 5 ng/ml). Most preferably, the formulation of the invention also includes fibroblast growth factor (pituitary), at a concentration of 5–400 ng/ml or, most preferably, 40 ng/ml,

2 Claims, 5 Drawing Sheets

Normal human cornea, 61y/o
Transplanted human cornea,
63 y/o -> 63 y/o, 2 weeks
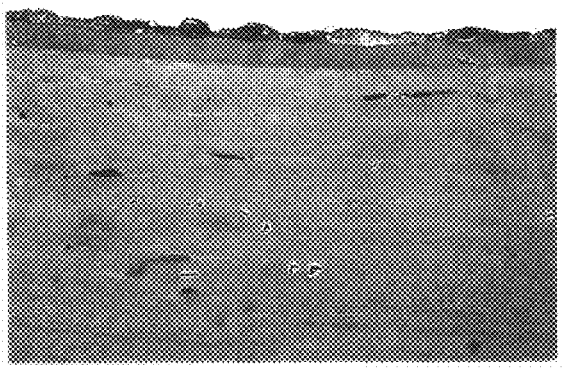
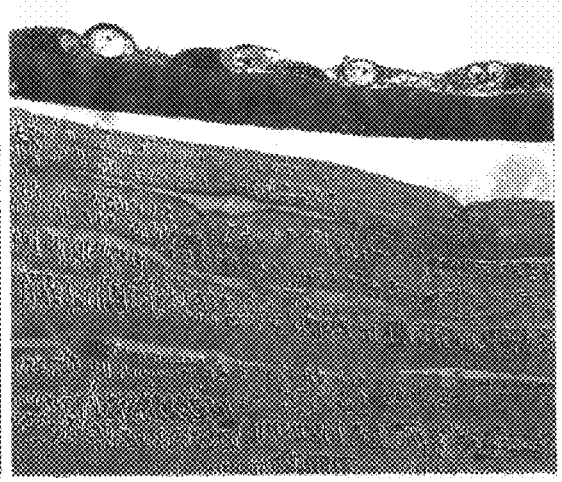
*FIG. 2A*   *FIG. 2B*

M199 + 10% serum
1% chondroitin sulfate
+ 1% collagen matrix

Chen's Medium Plastic

GROWTH MEDIUM FOR HUMAN CORNEAL ENDOTHELIAL CELLS

CROSS-REFERENCE TO RELATED APPLICATIONS

This application claims the priority of U.S. Provisional Patent Application No. 60/119,788 filed, Feb. 11, 1999 entitled GROWTH MEDIUM FOR HUMAN CORNEAL ENDOTHELIAL CELLS, the whole of which is hereby incorporated by reference herein.

STATEMENT REGARDING FEDERAL FUNDING

Part of the work leading to this invention was carried out with United States Government support provided under Grant No. NEI R01 EY05767 from the National Eye Institute. Therefore, the U.S. Government has certain rights in this invention.

BACKGROUND OF THE INVENTION

Corneal endothelial cells are different from vascular and pulmonary "endothelial cells" as they have a different embryonic tissue origin. Human corneal endothelial cells do not normally proliferate in vivo to replace those lost due to cell injury or death. Growth of these cells in culture is also extremely limited. This can be a serious problem as age, diseases such as glaucoma and diabetes, and ocular surgical procedures, such as laser vision correction and cataract extraction and intraocular lens implantation, cause an accelerated loss of these precious cells. There are no medical treatments for corneal diseases resulting from endothelial cell loss. Currently, corneal transplantation is the only way to restore normal vision.

The relative ability of corneal endothelial cells to proliferate in vivo and in culture appears to be a function of age; i.e., embryonic corneal endothelial cells and cells from neonates will proliferate much more readily than cells from children and adults. In a few cases, researchers have been able to culture cells from older donors, but growth has been supported by seeding the cells onto an artificial matrix, such as chondroitin sulfate/laminin, or onto extracellular matrix secreted by corneal endothelial cells from cows, one of a number of species whose corneal endothelial cells do grow readily in culture. A reliable way of supporting cell culture of human corneal endothelial cells would be highly desirable.

BRIEF SUMMARY OF THE INVENTION

A new formulation for a culture medium that can be used to overcome such difficulties has now been developed. In general, the invention is directed to a formulation for a growth medium for culturing cells of neural crest origin, most preferably corneal endothelial cells, or for accelerating the growth and proliferation of such cells. The formulation for the nutrient medium of the invention includes nerve growth factor, preferably at a concentration of 1–100 ng/ml and most preferably 20 ng/ml. The growth medium formulation preferably also includes epidermal growth factor (preferably at a concentration of 1–200 ng/ml and most preferably 5 ng/ml). Most preferably, the formulation of the invention also includes fibroblast growth factor, at a concentration of 5–400 ng/ml or, most preferably, 40 ng/ml.

A commercial growth medium, particularly a serum-free medium, forms a useful basis for the growth medium of the invention. The growth medium of the invention can be augmented with serum, e.g., fetal bovine serum, as needed. As is well known to cell culture specialists, a useful human cell growth medium preferably also includes added ascorbic acid, human lipids, antibiotics and cell viability stabilizers.

BRIEF DESCRIPTION OF THE DRAWINGS

Other features and advantages of the invention will be apparent from the following description of the preferred embodiments thereof and from the claims, taken in conjunction with the accompanying drawings, in which:

FIGS. 2A and 2B are micrographs showing comparative examples of the growth of human corneal endothelial cells from older donors using a prior art formulation (FIG. 2A) and the growth medium of the invention (FIG. 2B);

DETAILED DESCRIPTION OF THE INVENTION

The cornea is the "window" of the eye. Because it transmits light into the eye and protects the eye from the environment, normal vision requires a clear cornea. Corneal clarity results from the specific arrangements of fibrils in the stromal layer (see below) that permit light to be transmitted through the cornea rather than to be absorbed. If water is present in the stroma in excess amounts (corneal edema), the arrangement of these fibrils is disrupted, resulting in corneal clouding and loss of visual acuity.

Figure 1:
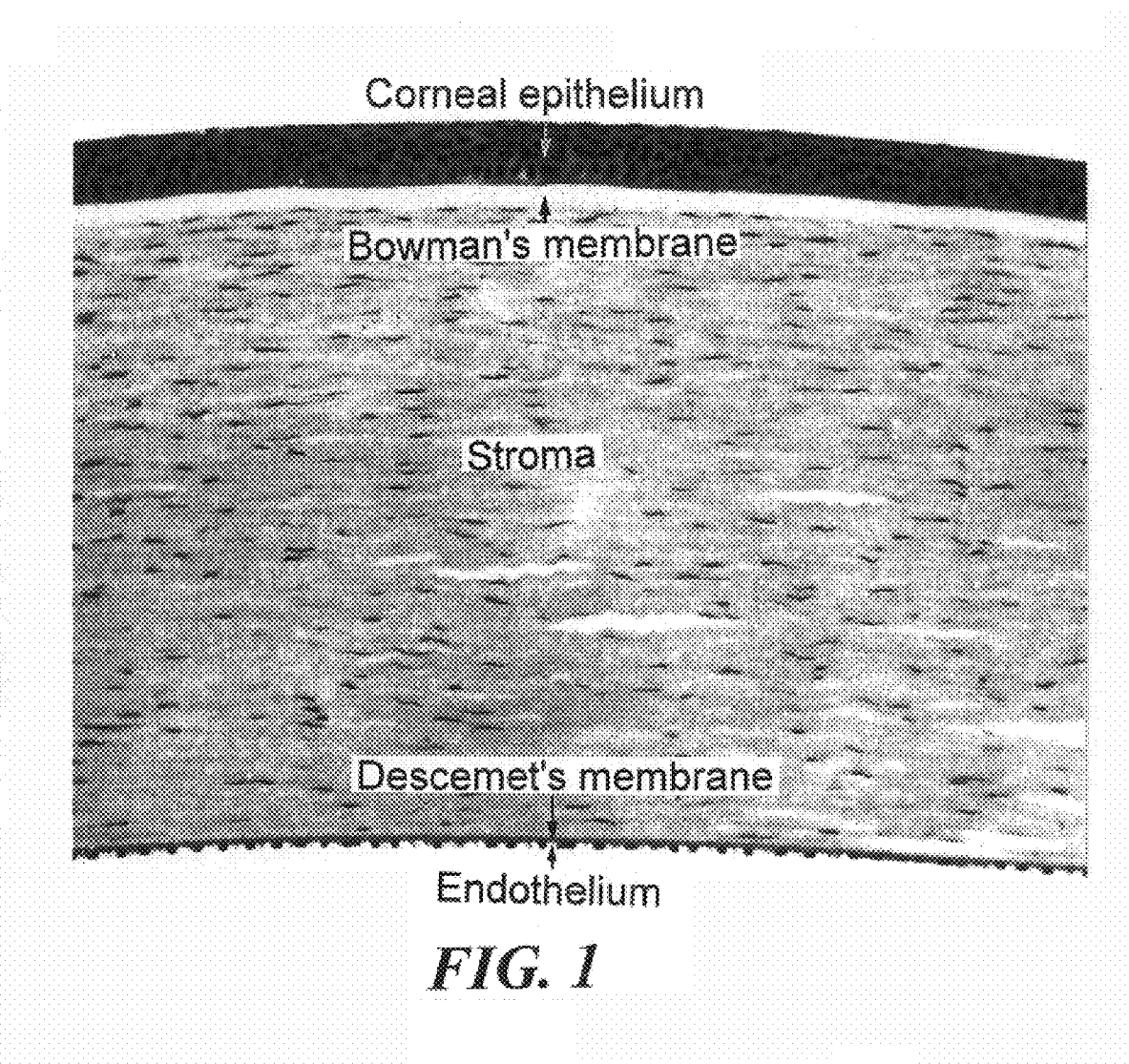
FIG. 1 is a cross-section of a cornea showing the orientation of the corneal layers.

As shown in FIG. 1, the cornea consists of four major layers. The epithelium is the outermost layer of the cornea. It is 5–7 cells thick and protects the eye in a manner similar to that of skin. It is bathed on the outside by tears. The stroma is the thick, gel-like middle layer that contains numerous long filaments separated from each other by molecules which tend to attract water. These filaments are precisely arranged to let light pass through the cornea without being bent or absorbed. The stroma also maintains the cornea in the curved shape required to focus light on the lens and the retina.

Bordering the interior of the stroma is a thick acellular layer known as Descemet's membrane. Endothelial cells secrete the gel-like material of this layer, and the composition of this layer differs from that of the stroma. Descemet's membrane is the substrate to which the endothelial cell layer is attached. The endothelium forms the innnermost layer of the cornea and is just one cell thick. The base of this cell layer is attached to Descemet's membrane and the surface is bathed by aqueous humor, the nutrient fluid that occupies the anterior chamber of the eye.

The cornea does not contain blood vessels and, as is such, nutrition of the corneal tissues occurs through both the ocular surface (which supplies the majority of oxygen) and the aqueous humor (which supplies all other nutrients). Cells of the endothelial monolayer permit slow percolation of aqueous humor through the intercellular spaces into the stroma, but the arrangement of these cells is sufficiently tight to form a barrier to prevent excess fluid from entering the stroma. Endothelial cells also contain an "ionic pump" in their plasma membrane that actively removes excess water from the stroma and returns it to the aqueous humor.

In spite of their importance in maintaining normal vision, corneal endothelial cells do not divide to replace dead or injured cells. So, throughout life, human endothelial cells are lost but not replaced. Instead, the remaining cells enlarge to cover the area formerly occupied by the dead or injured cells. As humans age, this gradual cell loss and enlargement of the remaining cells can cause breakdown of the endothelial barrier. In addition, diseases such as glaucoma and diabetes, and ocular surgical procedures, such as laser vision correction and cataract extraction and intraocular lens implantation, cause an accelerated loss of these precious cells. When cell density is reduced below a critical number (e.g., 500 cells/mm$^2$), water enters the stroma and disrupts the filament arrangement. This disruption causes the cornea to become cloudy. The visual loss resulting from corneal clouding is a form of blindness. Light can be perceived, but images are blurred, giving the appearance of looking through a dense fog. There are no medical treatments for corneal diseases resulting from endothelial cell loss. Currently, corneal transplantation is the only way to restore normal vision. The growth medium of the invention makes possible important new approachs to correcting these problems.

The optimal formulation of the growth medium of the invention was determined by dose-dependent testing of each ingredient on the viability and/or $^3$H-thymidine uptake (a measure of DNA synthesis/proliferation) of cultured rat corneal endothelial cells (a species whose cells grow well in culture). As the formulation developed, it was used to culture corneal endothelial cells from adult (>50 y.o.) human donors. For this culture, Descemet's membrane and attached endothelial cells were mechanically stripped from the donor cornea. The resulting tissue pieces were incubated for 1 hour in 0.2 mg/ml ethylenediaminetetraacetic acid (EDTA) to remove endothelial cells from Descemet's membrane. After centrifugation, the isolated cells were placed in 6-well tissue culture plates and incubated in culture medium at 37° C. in a 5% $CO_2$ humidified atmosphere. Medium was changed every other day. Cultured cells reached confluence in 7 to 14 days.

Prior to the development of this formulation, studies were conducted to test the ability of adult corneal endothelial cells to grow on an artificial matrix (1% chondroitin sulfate/1% collagen) and on bovine or rabbit corneal endothelial cell matrix. Better growth was obtained on the artificial matrix, but cell shape frequently differed from normal. Once the preferred formulation of the growth medium was determined, it was possible to grow cells from older adult (>50 y.o.) donors is directly on tissue culture plastic and still have them retain their normal polygonal shape. Thus, the use of the growth medium of the invention does not require coating the plastic with either artificial matrix or cell-derived matrix as is required by prior art formulations. FIG. 2 shows the results when endothelial cells from older corneal donors were cultured for the same period of time in either Medium 199 (GIBCO/BRL) supplemented with 10% fetal calf serum and 1% chondroitin sulfate and plated on a 1% collagen matrix (A) or were cultured with the growth medium of the invention on tissue culture plastic (B). Cells in (A) exhibit a lower density and abnormal, elongated morphology. Cells grown in the growth medium of the invention grow to a higher density and exhibit normal, polygonal morphology.

The preferred formulation of the growth medium of the invention has the following composition:
1. OptiMEM (containing insulin, transferrin, and selenium)—OptiMEM is a commercially available serum-free medium.
2. 8% fetal bovine serum (Hyclone) preferred range 125%.
3. 20 μg/ml ascorbic acid (Sigma)
4. 0.005% human lipids (Sigma)
5. 40 ng/ml fibroblast growth factor (pituitary) (Biomedical Research Technologies)—preferred range from 5–400 ng/ml
6. 5 ng/ml epidermal growth factor (mouse)—(Upstate Biotechnologies)—preferred range from 1–200 ng/ml
7. 20 ng/ml Nerve Growth Factor—(Biomedical Research Technologies) preferred range from 1–100 ng/ml
8. 0.08% chondroitin sulfate (Sigma)
9. 200 μg/ml calcium chloride (Sigma)
10. 50 μg/ml gentamycin (GibcoBRL)
11. RPMI-1640 Multiple Vitamin Solution- 1/100 (Sigma)
12. Antibiotic Antimycotic Solution- 1/100 (Sigma)

The growth medium of the invention differs from prior formulations in a number of specific ways. For example, the base medium used in the preferred formulation, OptiMEM (GIBCO/Life Technologies), contains ingredients important for supporting cell proliferation, such as insulin, transferrin, and selenium. Other nutrient media containing these three ingredients could substitute for OptiMEM. The growth medium of the invention also contains nerve growth factor, which is generally not included in culture media. Preferably, the medium of the invention contains a combination of nerve growth factor (NGF), epidermal growth factor (EGF) and fibroblast growth factor (FGF). Additionally, the preferred FGF concentration, at 10 ng/ml, is significantly lower than the 400 ng/ml FGF concentration in other conventional media, e.g., Englemann's medium.

The following example is presented to illustrate the advantages of the present invention and to assist one of ordinary skill in making and using the same. It is not intended in any way otherwise to limit the scope of the disclosure.

EXAMPLE 1

Evaluation of the morphology and function of cultured human corneal endothelial cells transplanted onto denuded Descemet's membrane of donor corneas.

Figure 3:
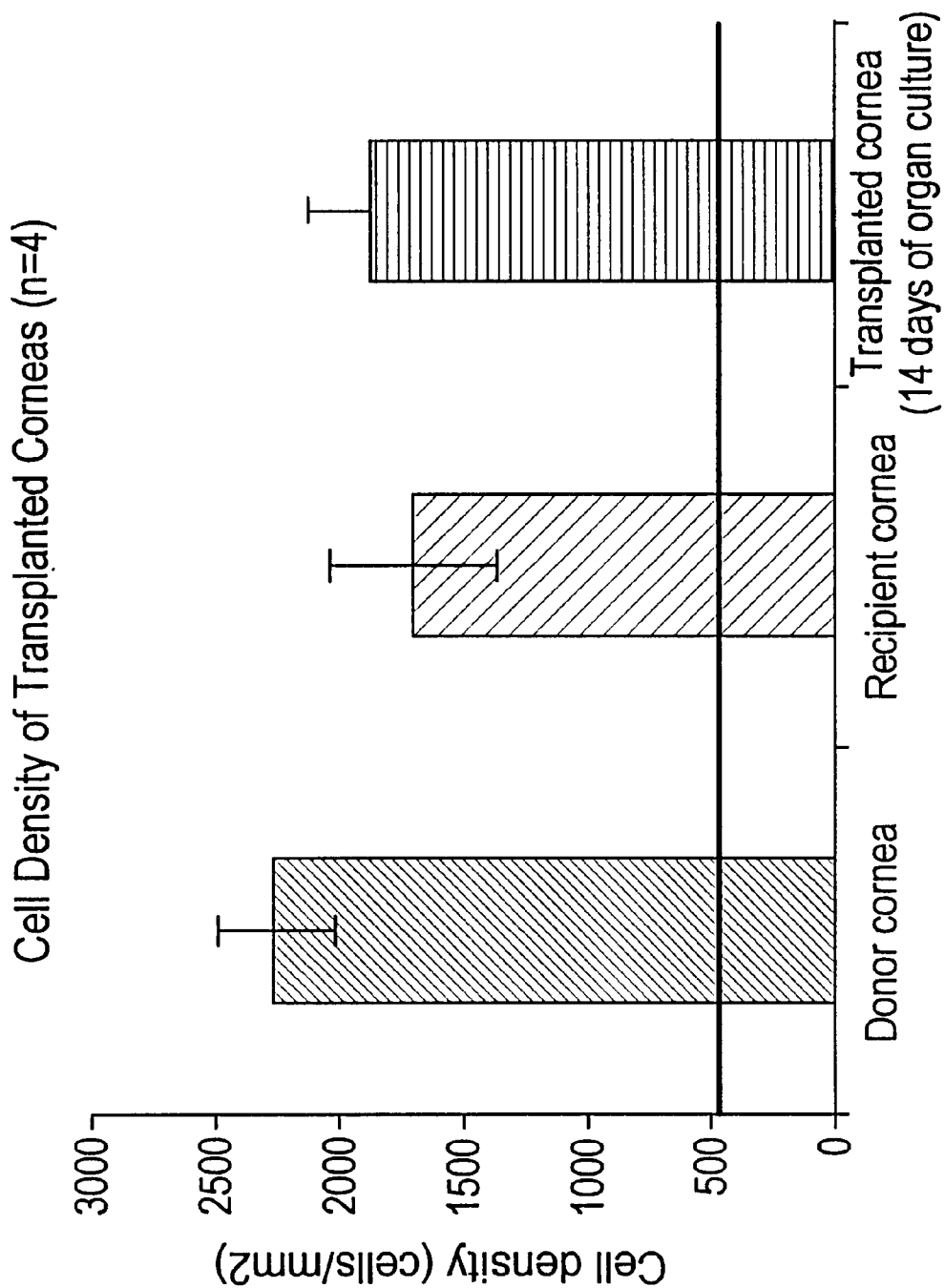
FIG. 3 is a bar graph showing cell density of transplanted corneas. A line drawn at 500 cells/mm$^2$ indicates the cell density below which there are insufficient cells to maintain corneal clarity.

Corneas from donors (52–80 years old) were obtained from an eye bank. Descemet's membrane was stripped and endothelial cells were removed by mild EDTA treatment. Cells, cultured in the preferred formulation of the culture medium, were identified by RT-PCR of collagen type VIII and keratin-12 and by morphology. Cells ($2.5 \times 10^5$) were seeded onto denuded Descemet's membrane from a second donor cornea. The cornea was incubated in culture for up to 1 month. Cell-cell contact of transplanted cells was evaluated by ZO-1 staining. Morphology and ultrastructure were examined by transmission electron microscopy. Pump function was tested by pachymetry after exposure to 200 μM ouabain. Cultured cells were identified as corneal endothelium by characteristic mRNA expression and morphology. The success rate of primary cultures, obtained from corneas stored <5 days after death, was about 99%. Cultures became confluent within one week. ZO-1 staining revealed normal cell shape and cell-cell contacts compared to normal corneas. Furthermore, as can be seen in FIG. 3, after 14 days in organ culture, the cell density (number of cells/mm$^2$) of the transplanted corneas is within the range of both the normal donor and normal recipient corneal cell densities.

Figure 4:
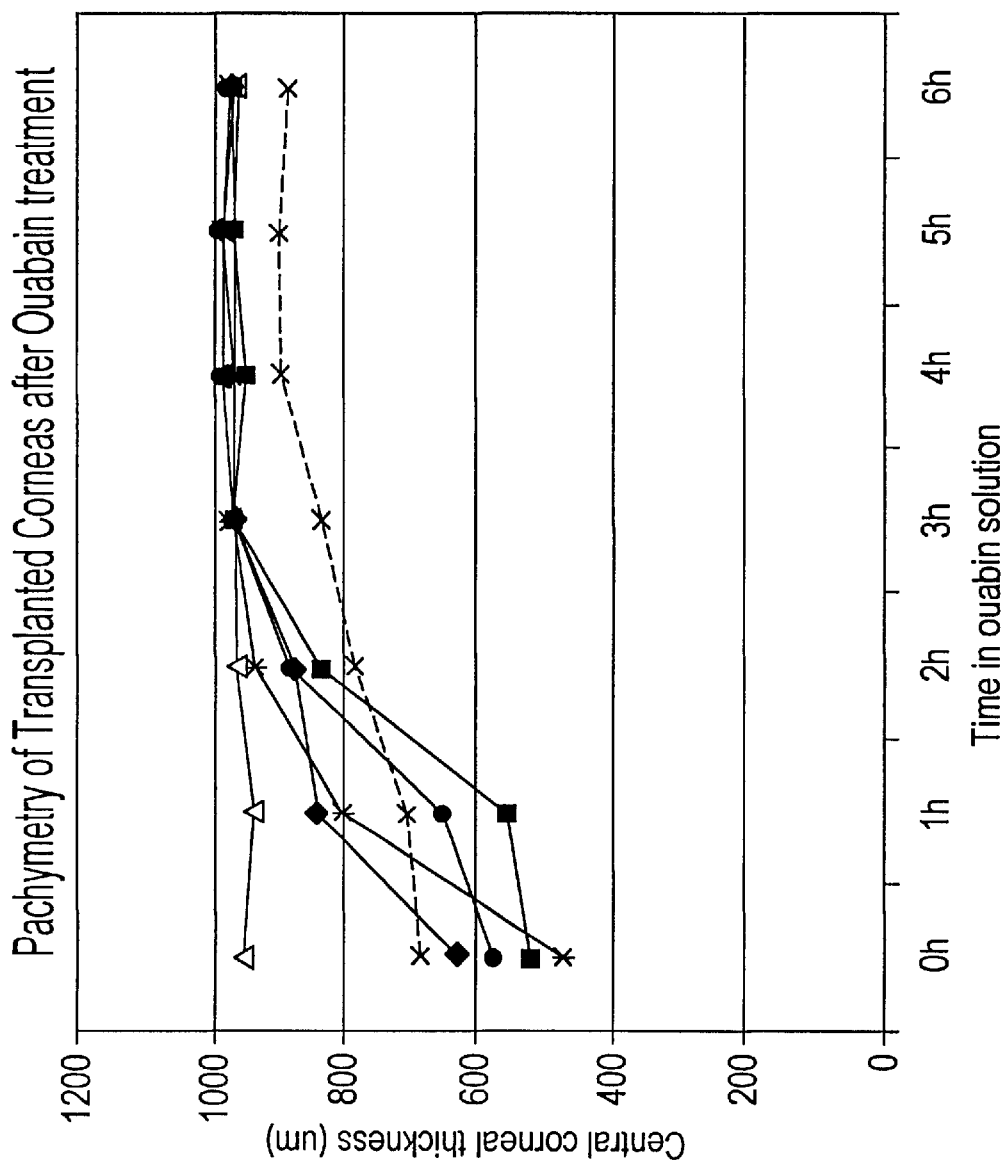
FIG. 4 is a graph showing pachymetry of transplanted corneas after ouabain treatment following 14 days in organ culture to illustrate that transplanted endothelium is functional.

With time, cell-substrate adhesion, cell-cell contact, and lateral interdigitation increased, and the cells rearranged to form a monolayer. When the endothelium is functional, it draws water out of the corneal stroma, resulting in a thin cornea. Ouabain, a cardiac glycoside, inhibits the function of the endothelial "ionic pump", causing an increase in corneal thickness. Upon exposure of the transplanted endothelium to ouabain, corneal thickness increased to a level equal to that of corneas denuded of endothelium, as measured by pachymetry. Referring to FIG. 4, pachymetry of transplanted corneas after ouabain treatment is graphically depicted. The open triangles represent thickness measurements from a cornea that was denuded of endothelial cells (negative control). Without a working "pump", this cornea remains thick (about 950 μm). The other symbols represent data from 5 corneas containing transplanted endothelial cells (transplants were maintained for 14 days in organ culture prior to thickness measurements). With exposure to ouabain, corneal thickness increased over a 2–3 hour period and reached the maximum thickness exhibited by the negative control. The ability of ouabain to increase corneal thickness indicates that the endothelium in the transplants was functional prior to ouabain addition.

Figure 5A:
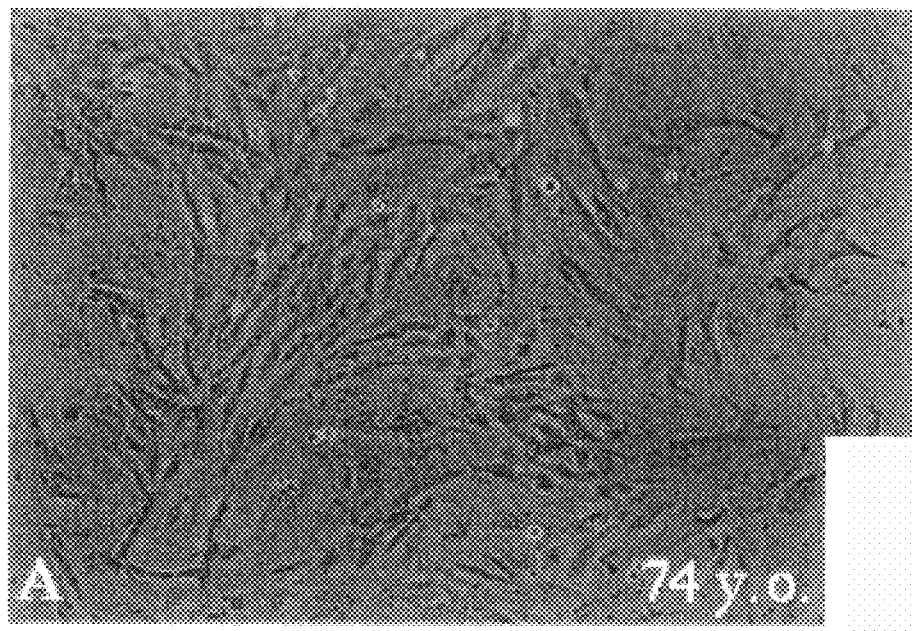
FIGS. 5A and 5B are micrographs comparing the morphology of normal and transplanted human corneal endothelium.
Figure 5B:
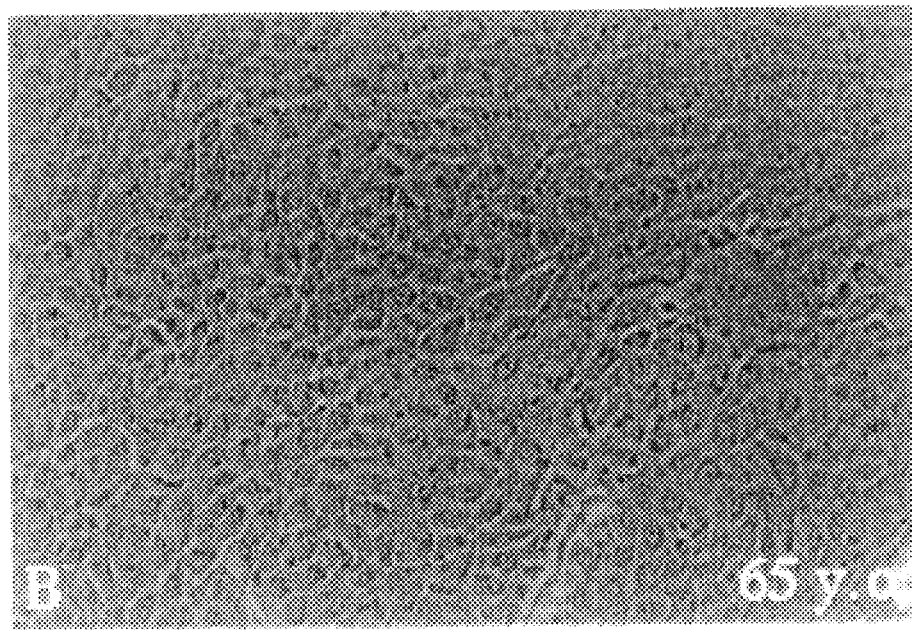

The various determinations described here show that the morphology and function of transplanted human corneal endothelial cells from older individuals are similar to those of normal endothelial cells. Referring to FIG. 5, thick plastic sections are shown comparing the morphology of normal and transplanted human corneal endothelium. The micorgraph on the left is a section of normal cornea obtained from a 61 year old donor. The micrograph on the right shows a cornea from a 63 year old donor that has been cultured in the growth medium of the invention. The transplanted cornea was photographed after 14 days in organ culture. After this time in culture, a normal monolayer of cells can be seen associated with the recipient Descemet's membrane. The density of the transplanted cells is similar to that of normal endothelium. (Original magnifications: Left micrograph= 40×, right micrograph=63×.)

Use

The growth medium of the invention may be applied to a patient's eye as topical drops or injected into the anterior chamber to induce transient proliferation of corneal endothelial cells in older individuals whose visual acuity is impaired due to low endothelial cell counts. Furthermore, cells from an older individual having low corneal endothelial cell density could be cultured in the growth medium of the invention to increase cell numbers. These could then be re-seeded onto the cornea of the patient to increase cell density and improve visual acuity.

The growth medium of the invention may be used as an irrigating solution (most probably not including serum) during anterior chamber surgical procedures to maintain the overall health and stability of the corneal endothelium (which can be compromised during these procedures) and to promote proliferation to replace cells damaged during the procedure. Furthermore, the growth medium of the invention (also without serum) would be a better supportive medium for the storage of donor corneas prior to transplantation than the prior art media.

The growth medium of the invention can support growth of human corneal endothelial cells for use in the development of "artificial" corneas. Up to this time, experimental artificial corneas have been prepared either with endothelial cells from species that grow better, such as mouse, or with SV40 transformed corneal endothelial cells.

With the use of the medium of the invention, researchers can now grow adult human corneal endothelial cells in culture without the need to seed cells onto artificial or cell-derived matrices. This will provide a ready supply of cells for molecular and cell biological studies that have been impossible to perform up to now.

Other Embodiments

The tissue embryonic origin of the corneal endothelium is neural crest. During fetal development, neural crest cells migrate and then differentiate to form many types of tissue. Many of the cell types formed from neural crest do not readily proliferate in vivo. The growth medium of the invention would be useful to induce proliferation in other ocular cells of similar origin, including, but not limited to, lacrimal gland acinar cells, ciliary body epithelium, corneal stromal keratocytes, skeletal muscle of the dorsal iris, and trabecular meshwork epithelium. Other non-ocular cells of similar embryonic origin should also proliferate upon exposure to this medium. Among non-ocular cell types of neural crest origin are sensory neurons, Schwann cells associated with the peripheral nervous system, and smooth muscle cells associated with the branchial arch arteries. Thus, the growth medium of the invention could be useful for repair of damaged tissue made up of the indicated cells, such as peripheral nerve damage and peripheral skeletal muscle damage, or for treating heart muscle after infarction.

The preferred formulation of the growth medium of the invention can be varied by those of skill in the art without compromising the positive effects of the invention as long as the formulation used includes nerve growth factor (NGF).

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A human cell growth medium formulation for culturing human cells of neural crest origin or for accelerating the growth and proliferation of human cells of neural crest origin, said growth medium formulation comprising:

insulin;

transferrin;

selenium;

1–100 ng/ml nerve growth factor;

5–400 ng/ml fibroblast growth factor (pituitary);

1–200 ng/ml epidermal growth factor;

1–25% fetal bovine serum;

10–50 μg/ml ascorbic acid;

0.001–0.01% human lipids;

0.01–0.12% chondroitin sulfate;

100–300 μg/ml calcium chloride;

10–100 μg/ml gentamycin;

RPMI-1640 multiple vitamin solution ($\frac{1}{50}$–$\frac{1}{200}$); and antibiotic antimycotic solution ($\frac{1}{50}$–$\frac{1}{200}$).

2. The growth medium formulation of claim 1, said growth medium formulation comprising about the following concentrations:

20 ng/ml nerve growth factor;

40 ng/ml fibroblast growth factor (pituitary);

5 ng/ml epidermal growth factor;

8% fetal bovine serum;
20 μg/ml ascorbic acid;
0.005% human lipids;
0.08% chondroitin sulfate;
200 μg/ml calcium chloride;
50 μg/ml gentamycin;
RPMI-1640 multiple vitamin solution (1/100); and
antibiotic antimycotic solution (1/100).

* * * * *

UNITED STATES PATENT AND TRADEMARK OFFICE
CERTIFICATE OF CORRECTION

PATENT NO. : 6,541,256 B1
APPLICATION NO. : 09/913218
DATED : April 1, 2003
INVENTOR(S) : Ko-Hua Chen et al.

Page 1 of 1

It is certified that error appears in the above-identified patent and that said Letters Patent is hereby corrected as shown below:

Title page, item (57) Abstract, line 13, "40 ng/ml," should read --40 ng/ml.--;

Column 2, line 63, "as is such" should read --as such--;

Column 3, line 55, "donors is directly" should read --donors directly--; and

Column 4, line 6, "125%" should read --1-25%--.

Signed and Sealed this

Tenth Day of July, 2007

JON W. DUDAS
*Director of the United States Patent and Trademark Office*